United States Patent
Newton et al.

(10) Patent No.: US 9,036,148 B2
(45) Date of Patent: *May 19, 2015

(54) ELECTROCHEMICAL DEPOSITION AND SPECTROSCOPIC ANALYSIS METHODS AND APPARATUS USING DIAMOND ELECTRODES

(75) Inventors: Mark Edward Newton, Warwickshire (GB); Julie Victoria MacPherson,
(Continued)

(73) Assignee: Element Six Technologies Limited (GB)

(*) Notice: Subject to any disclaimer, the term of this patent is extended or adjusted under 35 U.S.C. 154(b) by 0 days.
This patent is subject to a terminal disclaimer.

(21) Appl. No.: 14/115,055
(22) PCT Filed: May 11, 2012
(86) PCT No.: PCT/EP2012/058761
§ 371 (c)(1),
(2), (4) Date: Oct. 31, 2013

(87) PCT Pub. No.: WO2012/156307
PCT Pub. Date: Nov. 22, 2012

(65) Prior Publication Data
US 2014/0069815 A1    Mar. 13, 2014

Related U.S. Application Data

(60) Provisional application No. 61/487,501, filed on May 18, 2011.

(30) Foreign Application Priority Data

May 18, 2011    (GB) .................................. 1108342.5

(51) Int. Cl.
    *G01N 21/75*    (2006.01)
    (Continued)

(52) U.S. Cl.
    CPC .............. *G01N 21/75* (2013.01); *G01N 23/223* (2013.01); *G01N 27/48* (2013.01); *G01N 27/308* (2013.01); *C25D 21/12* (2013.01); *G01N 2223/076* (2013.01)

(58) Field of Classification Search
    CPC ..... G01N 21/75; G01N 21/12; G01N 23/223; G01N 27/48

USPC .......... 378/44, 45; 356/326, 432; 250/361 R, 250/370.09; 205/81; 204/406
See application file for complete search history.

(56) References Cited

U.S. PATENT DOCUMENTS

| | | | |
|---|---|---|---|
| 7,883,617 B2 | 2/2011 | Einaga et al. | |
| 2003/0170906 A1 | 9/2003 | Swain et al. | |
| 2010/0022416 A1* | 1/2010 | Flemming et al. .............. | 506/39 |

FOREIGN PATENT DOCUMENTS

CH    678662 A5    10/1991
(Continued)

OTHER PUBLICATIONS

Hutton, "Electrodeposition of Nickel Hydroxide Nanoparticles on Boron-Doped Diamond Electrodes for Oxidative Electrocatalysis," J. Phys. Chem. C, 2011, 115, 1649-1658.
(Continued)

*Primary Examiner* — Jennifer Dieterle
(74) *Attorney, Agent, or Firm* — Bryan Cave LLP

(57) ABSTRACT

A method of analyzing chemical species in a solution, the method comprising: providing an electrochemical deposition apparatus comprising a first electrode (2) formed of an electrically conductive diamond material and a second electrode (4); locating the first electrode in contact with a solution (8) to be analyzed and the second electrode in electrical contact with the solution to be analyzed; applying a potential difference between the first and second electrodes (2, 4) such that current flows between the first and second electrodes through the solution to be analyzed and chemical species are electrodeposited from the solution onto the first electrode; applying a spectroscopic analysis technique to the electro-deposited chemical species (M1, M2, M3) on the first electrode to generate spectroscopic data about the electro-deposited chemical species on the first electrode; and using the spectroscopic data to determine the type of chemical species electro-deposited on the first electrode. The spectroscopic analysis technique, which can be based on X-rays, fluorescent X-rays or gamma rays, is used in combination with stripping voltammetric measurement performed on the first electrode. The spectroscopic data can also be used in-situ calibration data for calibrating the reference potential used voltammetric measurements.

12 Claims, 4 Drawing Sheets

(72) Inventors: Warwickshire (GB); Patrick Robert Unwin, Warwickshire (GB); Timothy Peter Mollart, Oxfordshire (GB)

(51) Int. Cl.
*G01N 23/223* (2006.01)
*G01N 27/48* (2006.01)
*G01N 27/30* (2006.01)
*C25D 21/12* (2006.01)

(56) References Cited

FOREIGN PATENT DOCUMENTS

| | | | |
|---|---|---|---|
| EP | 1514090 | B1 | 3/2005 |
| EP | 1891423 | B1 | 2/2012 |
| GB | 2476237 | A | 6/2011 |
| JP | 2001091499 | A | 4/2001 |
| JP | 2005257320 | A | 9/2005 |
| JP | 2007040796 | A | 2/2007 |
| JP | 2010271236 | A | 12/2010 |
| JP | 2012127943 | A | 7/2012 |
| WO | 97/15820 | A1 | 5/1997 |
| WO | 03/085173 | A2 | 10/2003 |
| WO | 03/104765 | A2 | 12/2003 |
| WO | 2005/012894 | A1 | 2/2005 |
| WO | 2007/107844 | A1 | 9/2007 |
| WO | 2008/015435 | A1 | 2/2008 |
| WO | 2008/108124 | A1 | 9/2008 |

OTHER PUBLICATIONS

Wang et al., "Detection of Heavy Metal Ions in Water by High Resolution Surface Plasmon Resonance Spectroscopy Combined with Anodic Stripping Voltammetry," Analytical Chemistry, 2007, vol. 79, No. 12, 4427-4432.
Stotter et al., "Optical and Electrochemical Properties of Optically Transparent, Boron Doped Diamond Thin Films Deposited on Quartz," Analytical Chemistry, 2002, vol. 74, No. 23, 5924-5930.
Griesel et al., "Electro-Deposition as a Sample Preparation Technique for Total Reflection X-Ray Fluorescence Analysis," Spectrochimica Acta B, Atomic Spectroscopy, 2001, vol. 56, No. 11, 2107-2115.
Search Report for GB1208271.5 dated Aug. 30, 2012.
Search Report for GB1108342.5 dated Sep. 6, 2011.
International Search Report for PCT/EP2012/058761 dated Jul. 3, 2012.
International Search Report for PCT/EP2012/058038 dated Jun. 25, 2012.
Varney et al: "All-diamond micro-electrode arrays for neural recordings and diamond electrochemistry," Nano/Micro Engineered and Molecular Systems (NEMS), 2010 5th IEEE International Conference on IEEE, Piscataway, NJ, USA, Jan. 20, 2010, pp. 1116-1119.
Hutton et al: "Factors Controlling Stripping Voltammetry of Lead at Polycrystalline 80ron Doped Diamond Electrodes: New Insights from High-Resolution Microscopy," Analytical Chemistry, vol. 83, No. 3, Feb. 1, 2011, pp. 735-745.
Johnson et al., "In situ calibrated oxygen electrode," Sensors and Actuators B: Chemical, vol. 105, No. 2, 2005, 322-328.
McGAW et al., "A comparison of boron-doped diamond thin-film and Hg-coated glassy carbon electrodes for anodic stripping voltammetric determination of heavy metal ions in aqueous media," Analytica Chimica Acta, vol. 575, 2006, pp. 180-189.
Dai et al., "Measurements: Optically Transparent Carbon Electrodes," Analytical Chemistry, 15-22, Jan. 1, 2008.
Dai et al., "Optically Transparent Diamond Electrode for Use in IR Transmission Spectroelectrochemical Measurements," Analytical Chemistry, vol. 79, No. 19, Oct. 1, 2007.
Haymond et al., "Spectroelectrochemical responsiveness of a free-standing, boron-doped diamond, optically transparent electrode towards ferrocene," Analytica Chimica Acta, 500, 137-144 (2003).
Alov et al., "Total-reflection X-ray fluorescence study of electrochemical deposition of metals on a glass-ceramic carbon electrode surface," Spectrochimica Acta Part B, 56, 2117-2126 (2001).
Zhang et al., "A novel boron-doped diamond (BDD)-coated platinum mesh electrode for spectroelectrochemistry," Journal of Electroanalytical Chemistry 603, 135-141 (2007).
Ward Jones et al., "Stripping Analysis using Boron-Doped Diamond Electrodes," Current Analytical Chemistry, 4, 170-176 (2008).
Alov et al., "Formation of binary and ternary metal deposits on glass-ceramic carbon electrode surfaces: electron-probe X-ray microanalysis, total-reflection X-ray fluorescence analysis, X-ray photoelectron spectroscopy and scanning electron microscopy study," Spectrochimica Acta Part B, 58, 735-740 (2003).
Peeters et al., "Quantitative synchrotron micro-XRF study of CoTSPc and CuTSPc thin-films deposited on gold by cyclic voltammetry," Journal of Analytical Atomic Spectrometry, 22, 493-501 (2007).
Ritschel et al., "An electrochemical enrichment procedure for the determination of heavy metals by total-reflection X-ray fluorescence spectroscopy," Spectrochimica Acta Part B, 54, 1449-1454 (1999).
GB Search Report for GB1207688.1 dated Aug. 15, 2012.

\* cited by examiner (a)

(b)

(c)

ELECTROCHEMICAL DEPOSITION AND SPECTROSCOPIC ANALYSIS METHODS AND APPARATUS USING DIAMOND ELECTRODES

FIELD OF INVENTION

Certain embodiments of the present invention relate to the analysis of chemical species in solution using spectroscopic and, optionally, electrochemical sensing techniques and particularly using synthetic electrically conductive diamond electrodes in such techniques.

BACKGROUND OF INVENTION

Electrochemical sensors are well known. It has also been proposed in the prior art to provide a diamond based electrochemical sensor. Diamond can be doped with boron to form semi-conductive or fully metallic conductive material for use as an electrode. Diamond is also hard, inert, and has a very wide potential window making it a very desirable material for use as a sensing electrode for an electrochemical cell, particularly in harsh chemical, physical, and/or thermal environments which would degrade standard metal based electrochemical sensors. In addition, it is known that the surface of a boron doped diamond electrode may be functionalized to sense certain species in a solution adjacent the electrode.

One problem with using diamond in such applications is that diamond material is inherently difficult to manufacture and form into suitable geometries for sophisticated electrochemical analysis. To date, diamond electrodes utilized as sensing electrodes in an electrochemical cell have tended to be reasonably simple in construction and mostly comprise the use of a single piece of boron doped diamond configured to sense one physical parameter or chemical species at any one time. More complex arrangements have involved introducing one or more channels into a piece of boron doped diamond through which a solution can flow for performing electrochemical analysis. However, due to the inherent difficulties involved in manufacturing and forming diamond into multi-structural components, even apparently relatively simple target structures can represent a significant technical challenge.

In terms of prior art arrangements, WO 2005012894 describes a microelectrode comprising a diamond layer formed from electrically non-conducting diamond and containing one or more pin-like projections of electrically conducting diamond extending at least partially through the layer of non-conducting diamond and presenting areas of electrically conducting diamond at a front sensing surface. In contrast, WO2007107844 describes a microelectrode array comprising a body of diamond material including alternating layers of electrically conducting and electrically non-conducting diamond material and passages extending through the body of diamond material. In use, fluid flows through the passages and the electrically conducting layers present ring-shaped electrode surfaces within the passages in the body of diamond material.

More recently, it has been proposed that high aspect ratio boron doped diamond electrodes have improved sensing capability when compared with other boron doped diamond electrode arrangements. That is, it has been found to be highly advantageous to provide boron doped diamond electrodes which have a high length/width ratio at a sensing surface. Furthermore, it has been found that an array of high aspect ratio boron doped diamond electrodes providing a band sensor structure can be utilized to provide multiple sensing functions.

The previously described arrangements may comprise optically opaque, electrically conductive boron doped diamond electrodes spaced apart by optically transparent, non-conductive intrinsic diamond layers. The optically opaque, electrically conductive boron doped diamond electrodes can be driven to perform electrochemical measurements of species in aqueous solution. It has also been suggested that electrochemical techniques can also be combined with optical techniques such as spectroscopic measurements by using the non-conductive intrinsic diamond layers as an optical window as described in WO2007/107844. As such, electrochemical measurements can be performed at the optically opaque, electrically conductive boron doped diamond electrodes and optical measurements of the solution can be performed through non-conductive intrinsic diamond layers.

Swain et al. describe a combined electrochemistry-transmission spectroscopy technique for analysing chemical species in solution. The technique uses an electrochemical cell comprising an optically transparent carbon electrode (e.g. a thin film of boron-doped diamond on an optically transparent substrate), a thin solution layer, and an optical window mounted opposite the optically transparent carbon electrode such that transmission spectroscopy can be performed on species within the solution. The optically transparent carbon electrode is used to oxidize and reduce species in the solution. In situ IR and UV-visible spectroscopy is performed through the optically transparent carbon electrode to analyse dissolved species in the solution. Dissolved species which have different IR and UV-visible spectra in different oxidation states can be analysed. Although boron-doped diamond material is opaque at high boron concentrations, thin films of such material have a reasonable optical transparency. It is described that the ability to cross-correlate electrochemical and optical data may provide new insights into the mechanistic aspects of a wide variety of electrochemical phenomena including structure-function relationships of redox-active proteins and enzymes, studies of molecular absorption processes, and as a dual signal transduction method for chemical and biological sensing [see "Measurements: Optically Transparent Carbon Electrodes" Analytical Chemistry, 15-22, 1 Jan. 2008, "Optically Transparent Diamond Electrode for Use in IR Transmission Spectroelectrochemical Measurements" Analytical Chemistry, vol. 79, no. 19, Oct. 1, 2007, "Spectroelectrochemical responsiveness of a freestanding, boron-doped diamond, optically transparent electrode towards ferrocene" Analytica Chimica Acta 500, 137-144 (2003), and "Optical and Electrochemical Properties of Optically Transparent, Boron-Doped Diamond Thin Films Deposited on Quartz" Analytical Chemistry, vol. 74, no. 23, 1 Dec. 2002]. Zhang et al. have also reported the use of an optically transparent boron-doped diamond thin film electrode for performing combined electrochemistry-transmission spectroscopy analysis [see "A novel boron-doped diamond-coated platinum mesh electrode for spectroelectrochemistry" Journal of Electroanalytical Chemistry 603. 135-141 (2007)].

As an alternative to analysing chemical species while in solution as described above, one useful electro-chemical analysis technique involves applying a suitable voltage to a sensing electrode to electro-deposit chemical species out of solution onto the sensing electrode and then change the voltage to strip the species from the electrode. Different species strip from the electrode at different voltages. Measurement of electric current during stripping generates a series of peaks associated with different species stripping from the sensing electrode at different voltages. Such a stripping voltammetry technique can be used to analyse heavy metal content.

The use of a boron-doped diamond sensor in a stripping voltammetry technique has been described in U.S. Pat. No. 7,883,617B2 (University of Keio). Jones and Compton also describe the use of a boron-doped diamond sensor in stripping voltammetry techniques [see "Stripping Analysis using Boron-Doped Diamond Electrodes" Current Analytical Chemistry, 4, 170-176 (2008)]. This paper includes a review which covers work on a wide range of analytical applications including trace toxic metal measurement and enhancement techniques for stripping voltammetry at boron-doped diamond electrodes including the use of ultrasound energy, microwave radiation, lasers and microelectrode arrays. In the described applications a boron-doped diamond material is used for the working/sensing electrode in combination with standard counter and reference electrodes.

McGraw and Swain also describe using stripping voltammetry to analysis metal ions in solution using an electrochemical cell comprising a boron-doped diamond working electrode in combination with standard counter and reference electrodes (a carbon rod counter electrode and a silver/silver chloride reference electrode). It is concluded that boron-doped diamond is a viable alternative to Hg for the anodic stripping voltammetry determination of common metal ion contaminants [see "A comparison of boron-doped diamond thin-film and Hg-coated glassy carbon electrodes for anodic stripping voltammetric determination of heavy metal ions in aqueous media" Analytica Chimica Acta 575, 180-189 (2006)].

In addition to the stripping voltammetry techniques described above, it is also known to use spectroscopic techniques for analysing electro-deposited films. For example, Peeters et al describe the use of cyclic voltammetry to electrochemically deposit cobalt and copper species onto a gold electrode using a three electrode cell comprising a saturated calomel reference electrode, a carbon counter electrode, and a gold working electrode. The gold electrodes comprising electrochemically deposited cobalt and copper species were subsequently transferred to a synchrotron radiation X-ray fluorescence (SR-XRF) facility for SR-XRF analysis to determine the heterogeneity of the deposited layers and the concentrations of Co and Cu. A comparison of SR-XRF results with electrochemical data was used to investigate the mechanism of thin film growth of the cobalt and copper containing species [see "Quantitative synchrotron micro-XRF study of CoTSPc and CuTSPc thin-films deposited on gold by cyclic voltammetry" Journal of Analytical Atomic Spectrometry, 22, 493-501 (2007)].

Ritschel et al. describe electrodeposition of heavy metal species onto a niobium cathode. The niobium cathode comprising the electrodeposited heavy metal species is then transferred to a total reflection X-ray fluorescence (TXRF) spectrometer for TXRF analysis [see "An electrochemical enrichment procedure for the determination of heavy metals by total-reflection X-ray fluorescence spectroscopy" Spectrochimica Acta Part B, 54, 1449-1454 (1999)].

Alov et al. describe electrodeposition of heavy metal species onto a glass-ceramic carbon working electrode. A standard silver chloride reference electrode and a platinum counter electrode were used in the electrochemical cell. The glass-ceramic carbon working electrode comprising the electrodeposited heavy metal species is then transferred to a total reflection X-ray fluorescence (TXRF) spectrometer for TXRF analysis [see "Total-reflection X-ray fluorescence study of electrochemical deposition of metals on a glass-ceramic carbon electrode surface" Spectrochimica Acta Part B, 56, 2117-2126 (2001) and "Formation of binary and ternary metal deposits on glass-ceramic carbon electrode surfaces: electron-probe X-ray microanalysis, total-reflection X-ray fluorescence analysis, X-ray photoelectron spectroscopy and scanning electron microscopy study" Spectrochimica Acta Part B, 58, 735-740 (2003)].

WO 97/15820 discloses a combined surface plasmon resonance sensor and chemical electrode sensor. The electrode comprises a very thin layer of conducting or semi-conducting material which is suitable for supporting surface plasmon resonance. Materials suitable for supporting surface plasmon resonance are indicated to be reflective metals such as gold and silver although it is indicated that if these materials form a layer of 1000 angstroms or more then they will not support surface plasmon resonance. The electrode is used to electrochemical deposit species which are then stripped to generate stripping voltammetry data. The surface plasmon resonance analysis comprises reflecting a light beam off the electrode. The optical signal is used to determine an effective index of refraction and is a function of the index of refraction of materials deposited on the electrode and the thickness of the layer of material deposited on the electrode. While the surface plasmon resonance technique cannot on its own identify unknown types of chemical species it can be used in conjunction with electrochemical data to aid identification of unknown chemical species in a solution of interest. Furthermore, if the chemical species in a solution of interested are known, then the surface plasmon resonance technique can be used to determine the amount of material deposited and determine if material is left on the metallic electrode after electrochemical stripping.

The present inventors have identified a number of potential problems with the aforementioned techniques. For example, while Swain et al. and Zhang et al. have described the use of in-situ spectroscopic techniques through a transparent electrode in an electrochemical sensor to generate spectroscopic data which is complimentary to voltammetry data, the transmission IR and UV-visible spectroscopy techniques described therein are only suitable for analysis of chemical species in solution. They are not suitable for analysing species such as heavy metals electro-deposited on an electrode. Furthermore, as the species are not concentrated by electro-deposition onto an electrode surface then low concentrations of species in solution may be below the detection limit for certain spectroscopic techniques. Further still, such spectroscopic techniques only give information about chemical species in the bulk solution and do not give information about the surface of the sensor to establish, for example, when the surface of an electrode is clean or when minerals or amalgams form on an electrode surface.

In contrast, prior art stripping voltammetry techniques on diamond electrodes are advantageous for analysing species such as heavy metals which can be electro-deposited from solution as described by Jones, Compton, McGraw and Swain. However, species discrimination in multi-metal solutions can be a problem using such techniques since the peak positions can be overlapping in stripping voltammetry data. Furthermore, the use of standard reference and counter electrodes in such arrangements means that the electrochemical sensor is not robust to harsh chemical and physical environments, even if the diamond sensing electrode is robust to such conditions.

The problem of overlapping peaks in stripping voltammetry data can potentially be solved by applying the teachings of Peeters et al, Ritschel et al., and Alov et al. These groups have suggested electro-depositing films onto gold, niobium or glass-ceramic carbon working electrodes and then extracting the electrodes from the electro-deposition apparatus and transferring the coated electrodes to a suitable device for further analysis including, for example, electron-probe X-ray microanalysis, total-reflection X-ray fluorescence analysis, X-ray photoelectron spectroscopy and scanning electron microscopy. However, this technique requires the provision of multiple devices and the extraction of coated electrode components for subsequent analysis which may not be possible for field analysis and/or in remote sensing environments, e.g. down an oil well. Furthermore, the electrodes, particularly gold, can interfere with x-ray analysis techniques such as X-ray fluorescence analysis. Further still, the described electro-deposition apparatus uses electrodes which are not robust to harsh chemical and physical environments.

Similar comments apply having regard to WO97/15820 which discloses that very thin metal electrodes, particularly gold, are required for supporting surface plasmon resonance in combination with stripping voltammetry. Such electrodes can interfere with spectroscopic methods suitable for identifying unknown chemical species and the described surface plasmon resonance technique is not, in itself, able to uniquely identify unknown chemical species without also combining the optical data with suitably referenced electrochemical voltammetry data. Furthermore, the thin metal electrodes required for supporting surface plasmon resonance are not robust to harsh chemical and physical environments.

It is an aim of certain embodiments of the present invention to address one or more of the aforementioned problems. In particular, certain embodiments of the present invention provide a method and sensor configuration for monitoring low concentrations of a plurality of chemical species in complex chemical environments. Advantageous arrangements combine this functionality in a device which is relatively compact and is suitable for use in the field and/or in remote and/or harsh sensing environments such as for oil and gas applications.

SUMMARY OF INVENTION

A first aspect of the present invention provides a method of analysing chemical species in a solution, the method comprising:
- providing an electrochemical deposition apparatus comprising a first electrode formed of an electrically conductive diamond material and a second electrode;
- locating the first electrode in contact with a solution to be analysed and the second electrode in electrical contact with the solution to be analysed;
- applying a potential difference between the first and second electrodes such that current flows between the first and second electrodes through the solution to be analysed and chemical species are electro-deposited from the solution onto the first electrode;
- applying a spectroscopic analysis technique to the electro-deposited chemical species on the first electrode to generate spectroscopic data about the electro-deposited chemical species on the first electrode; and
- using the spectroscopic data to determine the type of chemical species electro-deposited on the first electrode.

Preferably, the spectroscopic analysis technique is applied in-situ within the electrochemical deposition apparatus. However, it is also envisaged that the electrochemical deposition step and the spectroscopic analysis step could be performed in two separate apparatus, an electrochemical deposition apparatus and a separate spectrometer. In such a two stage process, electrochemical deposition on the first electrode can be performed in the electrochemical deposition apparatus. The first electrode including the electrodeposited species can then be transferred to a spectrometer for spectroscopic analysis.

After spectroscopic analysis, the electrodeposited chemical species can be removed from the electrode and the electrode can be re-used. One method to do this is via acid cleaning or mechanical cleaning of the electrode. However, a more preferred route is to electrochemically strip the electrodeposited species from the electrode by changing the potential difference between the first and second electrodes in the electrochemical deposition apparatus to strip the electro-deposited chemical species from the first electrode.

While a two stage electrochemical deposition and spectroscopic method is envisaged as a possibility as outlined above, for many applications it is preferable, and in some cases essential, that the spectroscopic analysis is performed in situ within the electrochemical deposition apparatus. Accordingly, a second aspect of the present invention provides a sensor configured to perform the aforementioned method, the sensor comprising:
- a first electrode formed of an electrically conductive diamond material and configured to be located in contact with a solution to be analysed;
- a second electrode configured to be in electrical contact with the solution to be analysed;
- an electrical controller configured to apply a potential difference between the first and second electrodes to electro-deposit chemical species from the solution onto the first electrode, and
- a spectrometer configured to apply a spectroscopic analysis technique to the electro-deposited chemical species on the first electrode and generate spectroscopic data about the chemical species electro-deposited onto the first electrode after deposition and prior to stripping.

It has been found that the use of electrically conductive diamond material, particularly boron doped diamond material, it highly advantageous for the combined electrochemical deposition and spectroscopic analysis technique. While the use of a conductive diamond material as an electrode for electrochemical stripping voltammetry analysis is known in the art, it has not previously been suggested that a conductive diamond electrode is advantageous for use in an electrochemical deposition and spectroscopic analysis technique when compared with more standard metal electrodes. In a combined electrochemical deposition and spectroscopic analysis technique it has been found that the use of a conductive diamond electrode has two main advantages over standard metal electrodes:

(i) In the electrochemical deposition step it has been found that conductive diamond material outperforms standard metal electrodes in several respects:
   a. it has a broader potential window and can be driven at high voltages allowing electrochemically deposit of a wider range of chemical species at lower concentrations;
   b. it is inert and can thus be used in harsh physical and chemical environments which would damage standard metal electrodes;
   c. it can be more readily cleaned and re-used.

(ii) In the spectroscopic analysis step it has been found that conductive diamond material does not cause undue interference with the spectroscopic analysis of material deposited thereon. For example, in the analysis of metals it has been found that the use of a metal electrode can interfere with the spectroscopic analysis of metal species deposited thereon. Furthermore, the transparency of conductive diamond material to several spectroscopic analysis techniques, such as elemental analysis via x-ray fluorescence, allows the spectroscopic analysis to be performed through the diamond electrode allowing a sensor device to be configured with the spectrometer components behind the diamond electrode. This allows a sensor device to be configured into a probe which can be inserted into solutions to be analysed.

In light of the above, it is clear that diamond material has advantages over metal electrodes which are particular to the combined electrochemical deposition and spectroscopic analysis technique as described herein and are distinct from those which are applicable to electrochemical sensing such as by stripping voltammetry.

In certain arrangements the spectroscopic data alone is used to measure the type and, optionally, quantity of chemical species. In such arrangements, improved spectroscopic sensitivity is achieved by using the advantageous features of diamond material in terms of both improved electrochemical deposition and in terms of minimal spectroscopic interference.

Alternatively, the electrical controller is configured to change the applied potential difference between the first and second electrodes to strip the electro-deposited chemical species from the first electrode. In this case, the electric current may be measured during stripping of the electro-deposited chemical species thereby generating voltammetry data for the electro-deposited chemical species. That is, electrochemical sensing can be performed in combination with spectroscopic analysis. Using electrochemical sensor terminology the first electrode is a sensing or working electrode and the second electrode is a reference electrode. The voltammetry data can be used in combination with the spectroscopy data to determine the type and quantity of chemical species in the solution. For example, the spectroscopic data may be used to determine the type of chemical species deposited on the sensing electrode and the voltammetry data can be used to determine the quantity of chemical species deposited on the sensing electrode. In such arrangements, the spectroscopic data can be used to improved in-situ discrimination between electrochemical species and aid in resolving and assigning peaks in the voltammetry data. Accordingly, an electrochemical sensor can be provided which is suitable for monitoring low concentrations of a plurality of chemical species in complex chemical environments, which is relatively compact, and is suitable for use in the field and/or in remote sensing environments without requiring extraction and further analysis.

Accordingly, certain embodiments of the present invention relate to a combined electrochemical deposition and spectroscopic analysis method which utilizes synthetic electrically conductive diamond electrodes. Certain further embodiments relate to sensor device configurations which integrate electrochemical deposition apparatus and spectroscopic analysis apparatus such that the spectroscopic analysis can be performed in situ within the electrochemical deposition apparatus. Certain embodiments further include electrochemical stripping voltammetry to generate voltammetry data which can be used in combination with spectroscopic data to determine the type and quantity of chemical species in a solution. It has been found that the use of synthetic electrically conductive diamond electrodes in such combined electrochemical and spectroscopic techniques allows a wider range of chemical species to be detected at lower concentrations and with an improved ability to distinguish and identify a large number of different chemical species in complex solutions which comprising plurality of chemical species.

Various arrangements for integrating the spectrometer into the sensor are envisaged. For example, the sensor may comprise a window and the spectrometer can be configured to direct the spectroscopic analysis technique through the window towards a front surface of the chemical species electro-deposited onto the first electrode. Alternatively, the spectrometer may be configured to direct the spectroscopic analysis technique through the first electrode towards a rear surface of the chemical species electro-deposited onto the first electrode. Such an arrangement is advantageous in that the spectrometer can be mounted behind the first electrode such that only a single sensing surface is presented to the solution under testing. In such an arrangement, the material used for the first electrode must be transparent to the spectroscopic analysis technique. In this regard, the spectroscopic analysis technique is preferably an elemental analysis technique and, if the species deposited on the first electrode are opaque, may be a reflective technique. Examples of suitable techniques include optical techniques based on x-rays or gamma-rays, x-ray fluorescence (XRF) elemental analysis being preferred. Diamond material is advantageous for use with such techniques as it is transparent to such techniques and therefore will not unduly interfere with the spectroscopic analysis.

In addition to improving sensitivity and species discrimination, the spectroscopic data can also be used to assign peaks in the voltammetry data without requiring a standard reference electrode which maintains a fixed constant potential with respect to the sensing (i.e. working) electrode irrespective of the solution conditions. By way of background, the purpose of a reference electrode is usually to maintain a constant potential with respect to the working electrode. According to the Nernst equation the local concentration of redox active or potential determining ions will determine the reference electrode potential. Thus common reference electrodes such as the "saturated calomel electrode" and the "silver/silver chloride electrode" contain a metal coated in its sparingly soluble chloride salt in contact with a saturated concentration of chloride ions. In this way, the concentration of chloride ions next to the electrode surface is maintained at a fixed value irrespective of the solution conditions in which the electrode is placed. Commercial electrodes typically contain such an electrode housed in a glass body in contact with a solution filled with an excess of potassium chloride, separated from the main solution under test using a frit. For device fabrication this design may not be appropriate and so manufacturers often microfabricate Ag structures which they then chloridise to form a thin silver chloride coating. In solution the silver chloride dissolves to form a layer of chloride ions around the surface which can be approximated as being constant, however this is not as stable as a true reference electrode.

The issues with reference electrodes of the aforementioned type are:

(1) Fouling—if the electrode surface fouls it is problematic to clean the electrode by applying potential cleaning cycles without destroying the chemical identity of the reference electrode.

(2) In corrosive solution conditions, e.g. a high or low pH, again chemical degradation of the electrode means the reference electrode potential changes with time in the same solution.

(3) AgCl is light sensitive and can photodecompose again, effecting the stability of the electrode.

Although diamond is not a true reference electrode (as described above) the advantages of using diamond for the reference electrode are:

(1) It can be easily integrated into the diamond electrode fabrication procedure for the first (sensing) electrode.

(2) The diamond material is resistant to chemical and photo-degradation in all solutions, so once in solution, providing the solution composition remains effectively constant the electrode potential will remain constant.

(3) The diamond electrode can be efficiently cleaned using in-situ cleaning cycles (it is well documented in the literature that diamond electrodes can be cleaned using potentials pulses/cycles and/or heating)

Despite these advantageous features, the use of a diamond material as a reference electrode has one major problem in that the potential of the diamond reference (which is applied with respect to the sensing/working electrode) is unknown for different solutions. However, an in-situ spectrometer according to embodiments of the present invention can be used to calibrate the potential of the reference electrode. For example, in the case of case of anodic stripping voltammetry where a series of peaks are observed, although we know the potential they occur at with respect to a standard reference electrode, the reference potential for diamond is unknown and will vary from solution to solution. However, it is known that the sequence of metals observed in the voltammogram will not change, e.g. Cu is easier to oxidise than Pb which is which is easier than Zn etc. . . . . Hence by using a spectroscopic technique to independently determine the metal ions in solution the order of peaks can be correctly assigned.

Such an arrangement therefore allows the possibility to use a non-fixed reference electrode, i.e. a reference electrode which does not provide a fixed reference potential with respect to the sensing electrode irrespective of the solution conditions. Accordingly, a more robust reference electrode can be utilized. In a particularly preferred arrangement a doped diamond material, e.g. boron-doped diamond material, can be used for the reference electrode. Diamond electrode material is advantageous for the reasons given previously in this specification, e.g. in such an arrangement a doped diamond material can also be used for the sensing electrode and, if present, a counter electrode. As such, an electrochemical sensor can be configured to be self calibrating while also ensuring that only robust materials such as diamond materials are exposed to the solution under testing thus providing a device which is suitable for use in harsh sensing environments.

Certain embodiments of the present invention thus provide an electrochemical sensor with an integrated spectrometer configured to apply a spectroscopic analysis technique to the electro-deposited chemical species on the sensing electrode in-situ and generate spectroscopic data about the chemical species electro-deposited onto the sensing electrode after deposition and prior to stripping. Such an arrangement has several advantageous features including one or more of the following:

(1) Improved in-situ spectroscopic sensitivity by concentrating species using electro-deposition;
(2) Improved in-situ species discrimination in a multi-species solution by making comparative spectroscopic and electrochemical measurements;
(3) Internal calibration allowing the use of a more robust reference electrode.

Furthermore, the use of diamond as a window material for spectroscopic techniques such as XRF is advantageous since both intrinsic and heavily boron doped diamond are excellent x-ray windows. This contrast with none x-ray spectroscopic techniques such as UV-visible spectroscopy for which heavily boron doped diamond material is not transparent unless provided as a very thin film as described in prior art arrangements. As such, the use of doped diamond electrodes with x-ray or gamma-ray techniques is advantageous when compared with the use of doped diamond electrode with UV-visible spectroscopy as the material is inherently transparent to such techniques. Furthermore, the use of doped diamond electrodes with x-ray or gamma-ray techniques is advantageous when compared with the use of prior art metallic electrodes which interfere with such techniques. The use of a diamond electrode material is also advantageous as it does not form a mercury amalgam and thus enables mercury detection. A diamond electrode material is also advantageous in that a very high electrode potential can be applied to alter pH via proton or hydroxide generation. For metal ions which are complexed in solution, digests are normally performed to free them so they are available for subsequent reduction. One way to do this is to generate very strong acid (or base) conditions electrochemically. This is also useful for cleaning the electrode. As such, embodiments which utilize diamond electrodes have particular relevance to oil and gas operations when robust remotely operated sensors are needed, and environmental monitoring where mercury sensitivity, long term stability, and autonomous calibration is highly advantageous. That said, other x-ray transparent electrodes could be used for certain applications, e.g. thin film carbon or graphene on glass, thin film silicon, ITO, or thin film metals (trading x-ray transparency against conductivity).

The at least one electrode may be mounted on or over a supporting substrate. In an arrangement in which the spectrometer is configured to perform the spectroscopic analysis through such a substrate then the substrate material should also be selected to be transparent to the spectroscopic technique. Suitable substrates for x-ray techniques include AlN, $Al_2O_3$, $SiO_2$, BN, diamond, or other light element materials. Using a low atomic number material for the at least one electrode and substrate enables easy discrimination from target heavy (high atomic number) elements.

Using intrinsic optically transparent diamond as a substrate material and/or as a window material disposed around the at least one electrode at a sensing surface can also enable the use of other optical spectroscopic techniques in addition to, for example, x-ray techniques. Furthermore, although compact x-ray sources are commercially available, it is also envisaged that diamond material may be used as an in-situ x-ray source e.g. heavily boron doped diamond coated with copper. As such, diamond material may be utilized in an electrochemical sensor to combine a number of functional characteristics including one or more of: a boron doped diamond electrode material which is transparent to x-ray spectroscopic techniques; an intrinsic diamond material as a substrate or sensor surface material which is transparent to optical spectroscopic techniques; an in-situ x-ray source for x-ray spectroscopic techniques; a sensing surface which is robust to harsh chemical and thermal environments; and a similarly robust counter and/or reference electrode.

BRIEF DESCRIPTION OF THE DRAWINGS

For a better understanding of the present invention and to show how the same may be carried into effect, embodiments of the present invention will now be described by way of example only with reference to the accompanying drawings, in which.

DETAILED DESCRIPTION OF CERTAIN EMBODIMENTS

Figure 1:
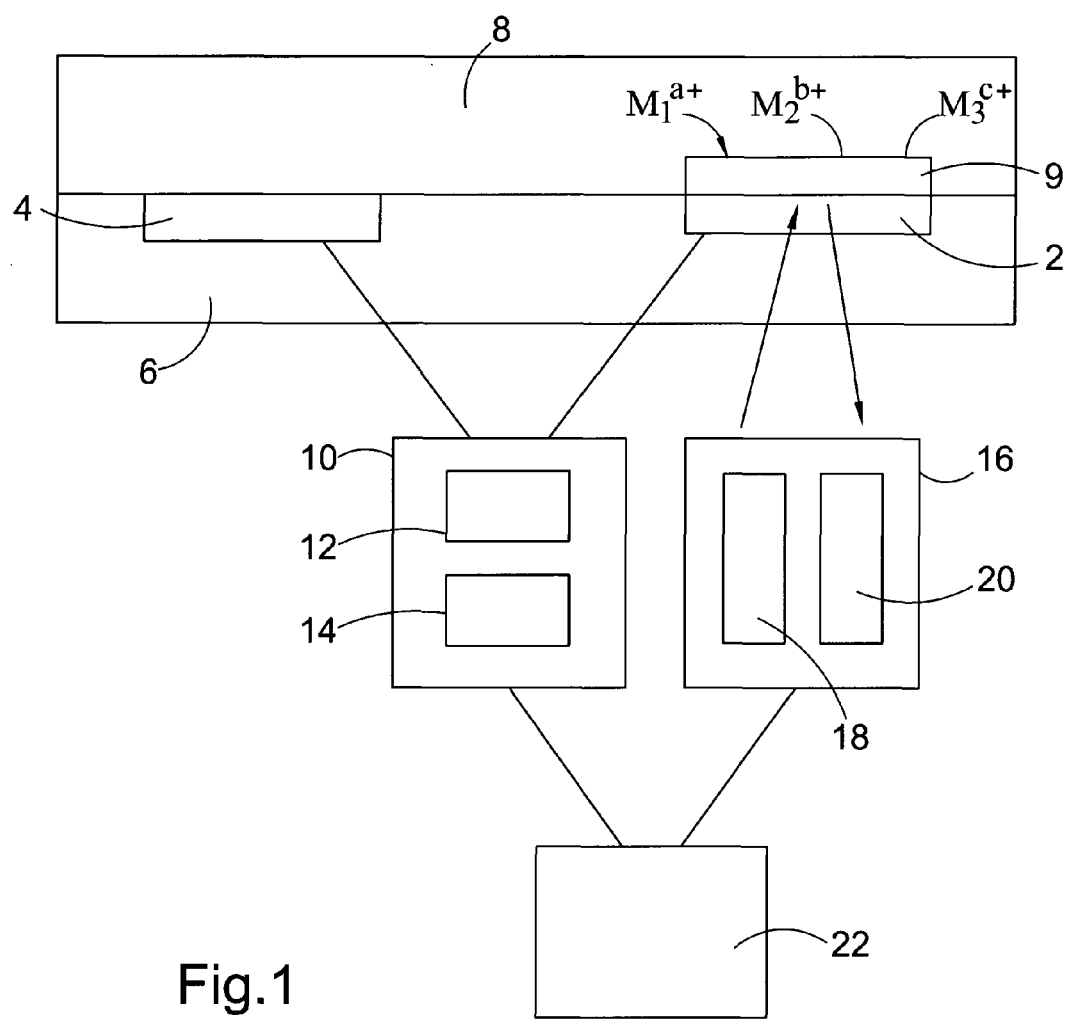
FIG. 1 is a schematic diagram of an electrochemical sensor according to an embodiment of the present invention.

FIG. 1 shows an electrochemical sensor which combines voltammetry and spectroscopic analysis techniques. The electrochemical sensor comprises two electrodes 2, 4 mounted in a support substrate 6. The electrodes 2, 4 are configured to be located in contact with a solution 8 in use. While the illustrated arrangement comprises two electrodes including a sensing electrode 2 and a reference electrode 4, it is to be noted that the supporting substrate may only comprise a sensing electrode 2 with a separate electrode being inserted into the solution to function as a reference electrode 4. In operation, metal species $M_1^{a+}$, $M_2^{b+}$, and $M_3^{c+}$ can be electro-deposited onto the sensing electrode 2 forming a solid metallic layer 9 comprising metal species $M_1$, $M_2$, and $M_3$.

The two electrodes 2, 4 are electrically coupled to an electrical controller 10 which comprises a voltage control unit 12 and a current measurement unit 14. The voltage control unit 12 is configured to apply a potential difference between the two electrodes 2, 4. A counter electrode (not shown) may also be provided if required.

Cyclic voltammetry (CV) refers to a procedure where the sensing electrode 2 is cycled first in one direction to a defined potential and then back again to a defined potential. Typically for stripping voltammetry the potential of the sensing electrode 2, rather than being cycled to a negative potential to reduce cations, is held at a constant potential for a defined time (for low concentrations it may be required to deposit for longer to get a measurable amount on the electrode surface) and then the potential is scanned positive or anodically to produce metal stripping peaks by oxidising all the metal—hence the technique is often referred to as anodic stripping voltammetry (ASV) or different pulse voltammetry (DPV) which means when scanning positively the electrode potential is pulsed to make the current reading more sensitive. Hence a combination of constant potential (deposition) and voltammetric techniques (stripping) are typically used in heavy metal detection using electrochemistry.

During stripping voltammetry the current measurement unit 14 measures current flow around the electrochemical circuit formed by the two electrodes 2, 4, the solution 8, the electrical controller 10 and the electrically couplings therebetween. Alternatively, where a counter electrode is provided, the current measurement unit 14 may measure current flow around the electrochemical circuit formed by the sensing electrodes 2, the counter electrode, the solution 8, the electrical controller 10 and the electrically couplings therebetween. Use of a counter electrode reduces the current at the reference electrode and improves its voltage stability. Oxidation (stripping) of metal species results in current flow at certain applied voltages relating to the oxidation potentials of the individual metal species. The magnitude of current flow can be plotted against the changing voltage to generate a stripping voltammogram comprising individual peaks corresponding to oxidation reactions for each of the metallic species. The position and size of each peak can be used to identify the type and quantity of metal species within the solution.

Deposition of species may be via direct or indirect electrochemistry. Direct electrodeposition occurs for a redox couple $A + ne^- \leftrightarrow B$ when A is converted to B through addition of electrons (reduction) whilst B is converted to A via the removal of electrons (oxidation). Typically both A and B are soluble in solution but there are instances where one species is in solid form and the other in solution as is the case for electrodeposition of a metal B from reduction of the associated cationic metal ion A. In contrast, for indirect electrodeposition the product being deposited is not part of a redox couple, as is the case above, but forms due to some precipitation reaction induced electrochemically. Typically this is likely to be an inorganic solid formed from two ions in solution, one which is present naturally, the other which is electrochemically generated. At a defined concentration the solubility product is exceeded causing the solid to precipitate out of solution. For example, if $Ni^{2+}$ ions are present in solution and $OH^-$ ions are generated electrochemically by the reduction of water this leads to the precipitation of nickel hydroxide on the electrode surface [see, for example, L. A. Hutton et al. "Electrodeposition of Nickel Hydroxide Nanoparticles on Boron-Doped Diamond Electrodes for Oxidative Electrocatalysis", J. Phy. Chem. 2010]. Decreasing the pH, e.g. by oxidising water to produce protons, may also be used to promote a reaction resulting in the formation of a solid species in solution. Additionally many inorganic solids have a pH dependant solubility for example under acidic conditions calcium carbonate is soluble however as the pH is increased the solubility will decrease causing calcium carbonate to precipitate out of solution. Hence precipitation reactions can be induced simply by changing pH electrochemically.

Thus far the described electrochemical sensor is the same as a standard stripping voltammeter in general construction. The illustrated electrochemical sensor differs from a standard stripping voltammeter in that it further comprises a spectrometer 16 configured to perform elemental analysis of solid species 9 which have been electro-deposited onto the sensing electrode 2. The spectrometer comprises an emitter 18 and a detector 20. In the illustrated arrangement, the spectrometer is configured to perform a spectroscopic analysis of the solid species 9 through the sensing electrode 2 and support substrate 6. As such, the electrode 2 and support substrate 6 should be made of a material which is transparent to the spectroscopic analysis. For example, the spectroscopic analysis may utilize an x-ray technique such as x-ray fluorescence (XRF) elemental analysis and the electrode 2 and substrate 6 may be made of a low atomic number material such as diamond. The electrode 2 may be formed of a boron doped diamond material such that it is electrically conductive while the support substrate 6 may be formed of an intrinsic diamond material. Both these materials are transparent to x-ray analysis. The intrinsic diamond material also has good transmittance for wavelengths from the infrared to the ultraviolet and thus further spectroscopic analysis of the solution 8 may be performed using these wavelengths through regions of the substrate 6 between the electrodes 2, 4.

The electrochemical sensor further comprises a data processor 22 which is configured to receive data from both the electrical controller 10 and the spectrometer 16. This data will be in the form of (optional) stripping voltammetry data from the electrical controller 10 and spectroscopic data from the spectrometer 16. Both types of data are capable of given information about the type and quantity of metal species electro-deposited onto the sensing electrode 2. However, in the case that two or more peaks in the stripping voltammetry data overlap for different species, the spectroscopic data can be utilized to determine the number and type of different species present to aid in interpretation of the stripping voltammetry data and function as a tool to deconvolute the data and correctly characterize the components within the solution. Alternatively, for certain applications the electrical controller may function only as a means of depositing chemical species from solution for spectroscopic analysis. In this case, qualitative spectroscopy can identify the type of species present whereas quantitative spectroscopy can determine both the type and quantity of species. Use of a diamond material for the electrode 2 is advantageous in this regard as a large potential can be applied to electro-deposit a large range of target species for spectroscopic analysis. Target species can be deposited via direct or indirect electrochemistry as discussed earlier.

Figure 2:
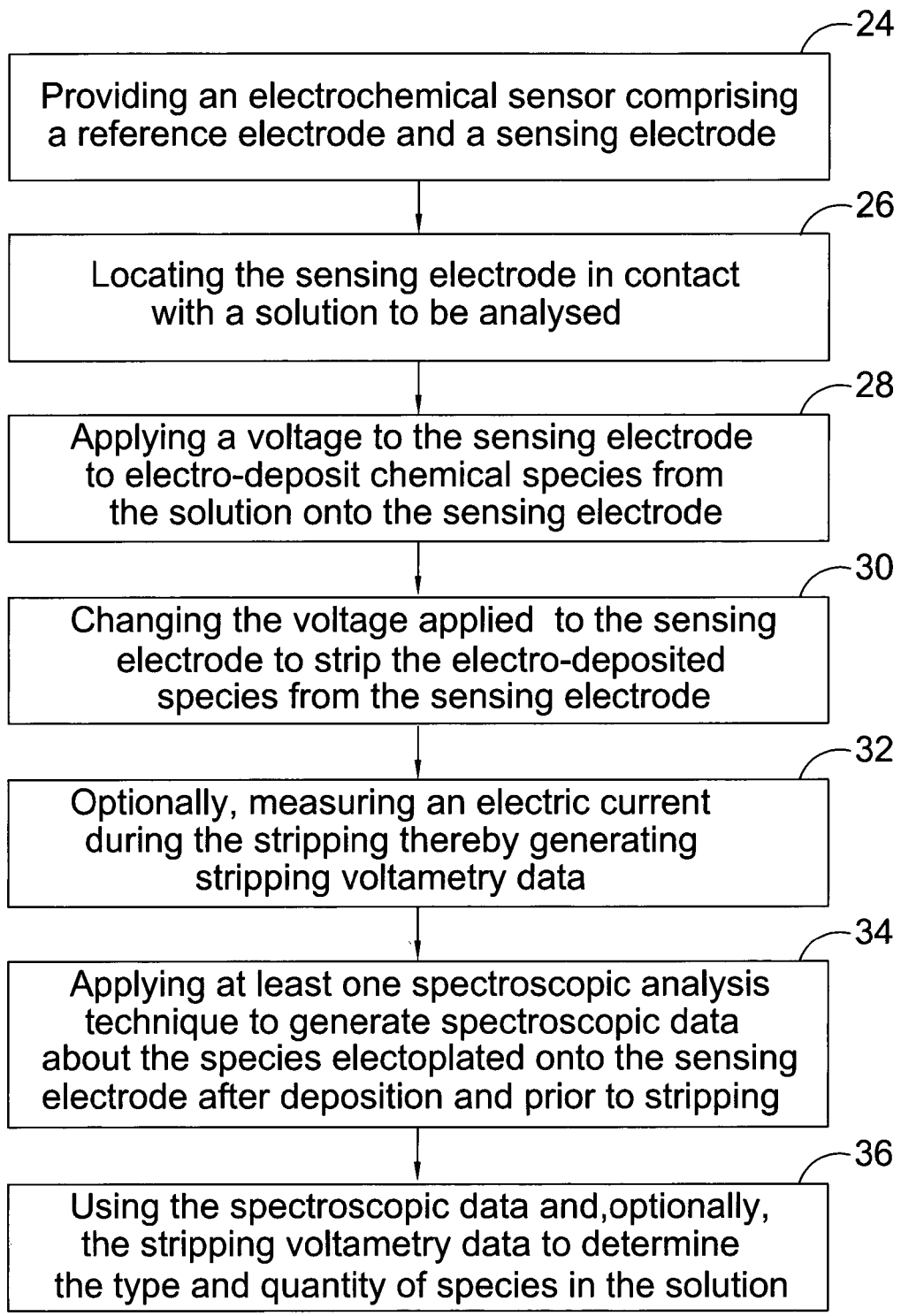
FIG. 2 is a flow chart illustrating a method of measuring target species using the electrochemical sensor shown in FIG. 1.

FIG. 2 is a flow chart illustrating a method of measuring target species using the electrochemical sensor shown in FIG. 1. The method comprises:
- providing an electrochemical sensor comprising a reference electrode and a sensing electrode (24);
- locating the sensing electrode in contact with a solution to be analysed (26);
- applying a voltage to the sensing electrode to electro-deposit chemical species from the solution onto the sensing electrode (28);
- changing the voltage applied to the sensing electrode to strip the electro-deposited chemical species from the sensing electrode (30);
- optionally, measuring an electric current during the electro-stripping thereby generating stripping voltametry data (32);
- applying at least one spectroscopic analysis technique to generate spectroscopic data about the chemical species electro-deposited onto the at least one electrode after depositing and prior to stripping (34); and
- using the spectroscopic data and, optionally, the stripping voltammetry data to determine the type and quantity of chemical species in the solution (36).

The above procedure can be repeated, and data from one cycle can be combined with data from another cycle if required. For example, spectroscopic and voltammetric data may be acquired on separate cycles. Alternatively, repeat cycles may use different voltage/current/dwell parameters, for example to assist in peak separation.

Figure 3:
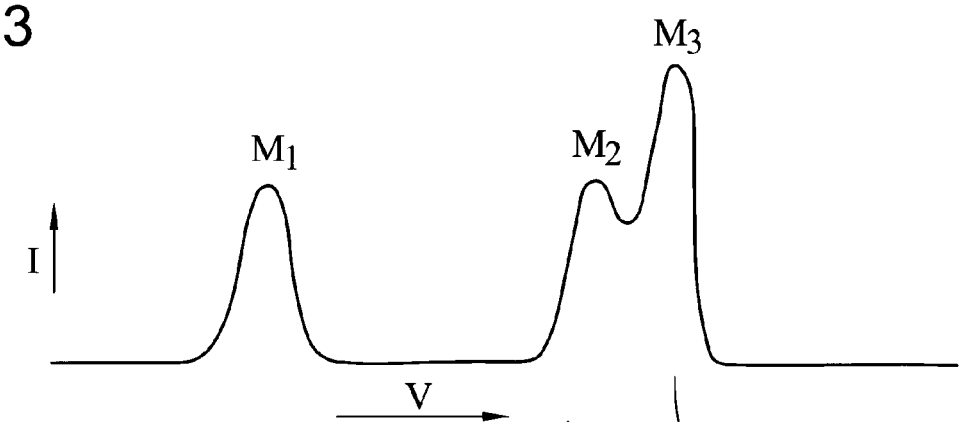
FIGS. 3a to 3c illustrate the type of data generated using the method shown in FIG. 2.
Figure 3:
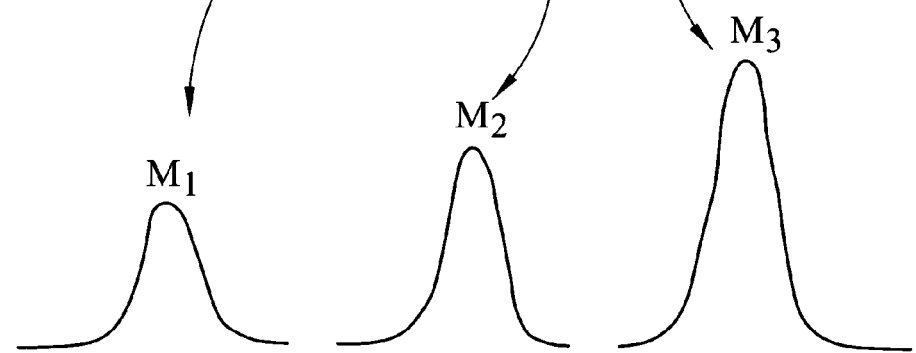
Figure 3:
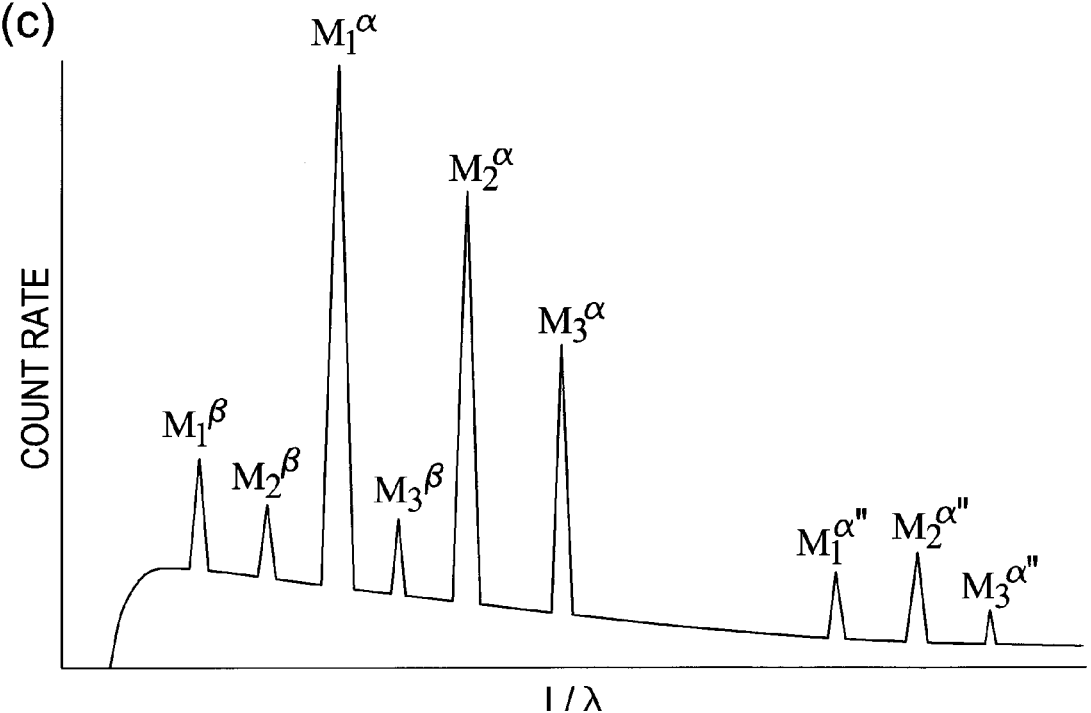

FIGS. 3a to 3c illustrate an example of data generated using the method shown in FIG. 2. FIG. 3a shows a stripping voltammogram generated by the electrical controller. The stripping voltammogram comprises oxidation peaks for three species $M_1$, $M_2$, and $M_3$. Although there is some overlap between the peaks, they are sufficiently separated that the stripping voltammogram can be deconvoluted into three separate voltammograms, one for each species as illustrated in FIG. 3b. These voltammograms can be used to identify the type and quantity of each species by peak location and area measurements. In practice, this can be done numerically or by generating pictorial representations of the voltammetry data. For example, the composite voltammogram can be deconvoluted using Fourier analysis techniques. Peak locations can be compared to a reference potential to identify different target species of interest. The peaks can be numerically integrated in order to determine quantitative information about the individual species. These techniques are known to those skilled in the art.

Figure 4:
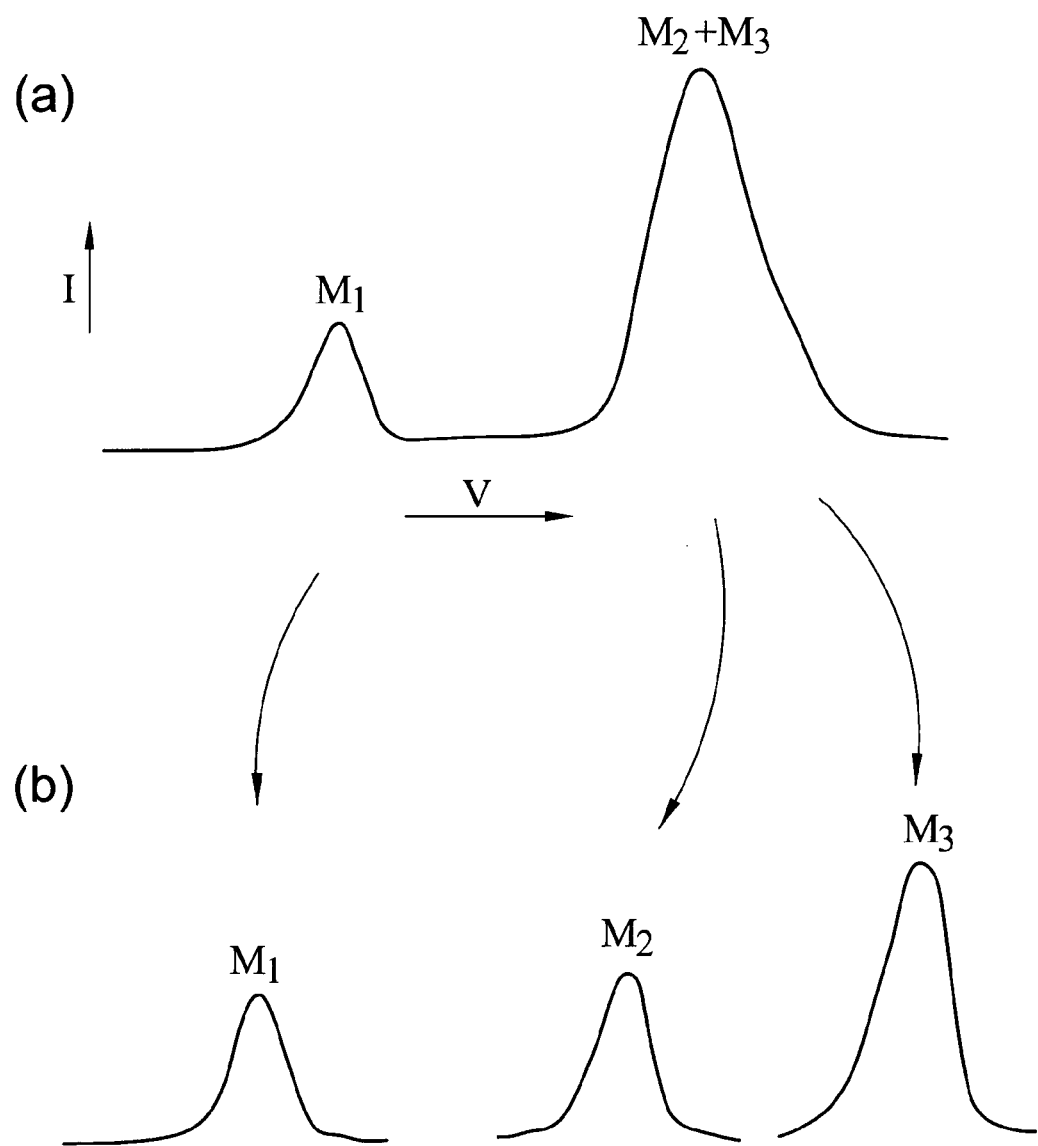
FIGS. 4a to 4c illustrate another example of the type of data generated using the method shown in FIG. 2.

In addition to the voltammetry data discussed above, FIG. 3c illustrates an XRF spectrum obtained by the spectrometer 16. The spectrum $K_\alpha$, $K_\beta$, and second order $K_\alpha''$ lines for the three metal species previously discussed. This spectroscopic information can also be used to determine the type and quantity of species electro-deposited on the sensing electrode 2. In the event that the target species are individually identifiable and quantifiable in the stripping voltammetry data, this spectroscopic data may be somewhat superfluous and may merely serve to confirm results obtain via stripping voltammetry. However, in the case that one or more of the target species have overlapping peak in the stripping voltammetry data such that the data cannot be readily be deconvoluted, the spectroscopic data can either be used as a means to deconvolute the voltammetry data or otherwise used instead of the voltammetry data to identify and quantify individual target species. For example, FIG. 4a shows a stripping voltammogram for three target species $M_1$, $M_2$, and $M_3$ where the peaks for species $M_2$ and $M_3$ completely overlap. Decovolution of this voltamogram without any other information may result in the erroneous identification of only two species, e.g. $M_1$ and $M_2$ only or $M_1$ and $M_3$ only, or otherwise give an ambiguous result indicating that $M_2$ and/or $M_3$ may be present. In this case, spectroscopic data as indicated in FIG. 3c can be used to correctly deconvolute the composite voltammogram illustrated in FIG. 4a into its three constituent parts as shown in FIG. 4(b). Alternatively, the spectroscopic data could be used on its own, the electrical controller merely being utilized as a means of depositing species for spectroscopic analysis. However, in practice the voltammetry data and the spectroscopic data can provide complimentary information. For example, the spectroscopic data can give elemental information which may not be resolved in the voltammetry data whereas the voltammetry data may give information relating to the oxidative state of species within the solution which cannot be identified from the spectroscopic data. The voltammetry data will also be more sensitive to species present at low concentration.

Alternatively, or in addition to, the above, if a non-fixed reference electrode is utilized, such as a doped diamond reference electrode, the spectroscopic data may be used to assign peaks in the stripping voltammogram when no fixed reference potential is present. In this case, although the potential at which individual peaks will vary, the sequence of species observed in the stripping voltommogram will be fixed. As such, by identifying the species present in the solution using spectroscopy, the identified species can be assigned to the stripping voltammetry peaks given the known sequence.

As previously discussed, the use of a diamond electrode material in combination with an x-ray spectroscopic analysis technique is considered to be particularly preferable for implementing the present invention. Compact x-ray sources are commercially available. Alternatively, the diamond material may be used as an in-situ x-ray source, e.g. by coating a boron doped diamond material with a metal such as copper to form an x-ray source.

The integration of a spectrometer into an electrochemical sensor in the manner described herein will increase functionality and performance in terms of resolution and sensitivity for analysing solutions which contain a plurality of different target species of interest. Previously, for solutions which comprise a number of different species having overlapping voltammetry peaks, for example a number of heavy metal species having similar electrochemical potentials, it may only have been possible to determine the total species content, e.g. the total heavy metal content. In contrast, embodiments of the present invention allow identification and quantification of a large range of different species in a single solution even when voltammetry peaks overlap.

Various different electrode structures may be utilized with the combined electrochemical/spectroscopic techniques described herein. Some examples of prior art diamond electrode arrangements are discussed in the background section. In addition to the provision of a diamond sensing electrode, as previously described it is also advantageous to provide a diamond reference electrode. If the reference electrode is made of, for example, Ag/AgCl or $Hg/Hg_2Cl_2$ (common reference electrodes) then the reference electrode may be contaminated or attacked in aggressive environments. Using a diamond reference is preferable as it will not be etched and has a high dimensional stability in aggressive chemical/ physical environments. Providing an integrated spectrometer to aid in assigning voltammetry allows such a non-fixed potential reference electrode to be utilized.

Other useful techniques may be combined with the electrochemical/spectroscopic techniques described herein. For example, differential potential pulse programmes can be used to increase sensitivity. Furthermore, the temperature of the sensing electrode can be changed to alter mass transport, reaction kinetics, and alloy formation. For example, heating during stripping voltammetry can aid in increasing peak signals. Heating during deposition can aid formation of better alloys and can also increase mass transport, shortening deposition times and/or increasing deposition to within the detection sensitivity of spectroscopic techniques such as XRF. Accordingly, in certain arrangements configured to detect very low concentrations of chemical species in solution a heater may be provided within the electrochemical sensor for heating the sensing electrode to increase deposition to within the limits of the spectroscopic analysis technique. The use of diamond material for the sensing electrode is also useful in this regard as diamond material can be heated and cooled very quickly. The high electrode potential of diamond material can also be utilized to alter pH via electrochemical generation. For metal ions which are complexed in solution, digests are normally performed to free them so they are available for subsequent reduction. One way to do this is to generate very strong acid (or base) conditions electrochemically. This is also useful for cleaning the electrode. Other cleaning techniques may involve abrasive cleaning and/or heating. Again, use of a diamond material is advantageous in this regard as the diamond material is robust to abrasive, chemical, and/or heat treatments for cleaning and thus a good sensing surface can be re-generated between analysis cycles. In order to ensure that the sensing electrode is clean after a sensing cycle and prior to initiation of a further cycle an additional spectroscopic analysis and/or an electro-stripping cycle may be applied to determine if the sensing electrode is clean. For example, residual chemical species adhered to the electrode may be evident in voltammetry and/or spectroscopic data generated during such a cleanliness checking step. If so, a cleaning cycle can be performed. A further spectroscopic analysis and/or an electro-stripping cycle may than be applied to confirm that the sensing electrode is sufficiently clean for further use. As such, cleaning and checking of electrode surfaces can be performed in-situ.

Embodiments of the present invention thus provide a number of advantageous features including one or more of the following:

1. Species discrimination in multi-species solutions, even where peak positions are overlapping in anodic stripping voltammetry.

2. In-situ calibration of species even when there is an inter-dependency of peak area in voltammetry data due to inter-metallic formations or amalgams which may otherwise make specific species discrimination difficult.

3. Creating a reference for assigning peaks in voltammetric data even when a standard reference electrode is not use, thus allowing a more robust reference electrode to be utilized such as one made of a diamond material. Certain embodiments can provide an autonomous quantification/calibration of the sensor device in-situ.

4. Detecting mercury in an environmentally friendly manner, since existing electrodes typically use gold mercury amalgams which are considered to be environmentally unsound.

5. In-situ cleaning of the surface of electrodes, prior to use and after a metal deposition/stripping cycle has been completed thus avoiding the requirement to prepare the electrode surfaces ex-situ prior to each measurement, which may be a requirement of current commercial sensors based on gold mercury amalgams.

6. The ability to detect and quantify a large range of chemical species in complex solution environments including, for example, calcium ("scaling capacity"), copper, zinc, cadmium, mercury, lead, arsenic, aluminium, antinomy, iodine, sulphur, selenium, tellurium, uranium, etc.

While this invention has been particularly shown and described with reference to preferred embodiments, it will be understood to those skilled in the art that various changes in form and detail may be made without departing from the scope of the invention as defined by the appendant claims.

The invention claimed is:

1. A method of analysing chemical species in a solution, the method comprising:
    providing an electrochemical deposition apparatus comprising a first electrode formed of an electrically conductive diamond material and a second electrode;
    locating the first electrode in contact with a solution to be analysed and the second electrode in electrical contact with the solution to be analysed;
    applying a potential difference between the first and second electrodes such that current flows between the first and second electrodes through the solution to be analysed and chemical species are electro-deposited from the solution onto the first electrode;
    applying a spectroscopic analysis technique comprising x-ray fluorescence elemental analysis to the electro-deposited chemical species on the first electrode to generate spectroscopic data about the electro-deposited chemical species on the first electrode;
    using the spectroscopic data to determine the type of chemical species electro-deposited on the first electrode; and
    using the spectroscopic data to determine the quantity of chemical species in the solution.

2. A method according to claim 1, wherein the spectroscopic analysis technique is applied in-situ within the electrochemical deposition apparatus.

3. A method according to claim 1, further comprising changing the potential difference to strip the electro-deposited chemical species from the first electrode.

4. A method according to claim 3, further comprising measuring the electric current flowing between the first and second electrodes during stripping of the electro-deposited chemical species thereby generating voltammetry data for the electro-deposited chemical species, the first electrode functioning as an electrochemical sensing electrode and the second electrode functioning as a reference electrode.

5. A sensor comprising:
    a first electrode formed of an electrically conductive diamond material and configured to be located in contact with a solution to be analysed;
    a second electrode configured to be in electrical contact with the solution to be analysed;
    an electrical controller configured to apply a potential difference between the first and second electrodes to electro-deposit chemical species from the solution onto the first electrode,
    a spectrometer configured to apply a spectroscopic analysis technique comprising x-ray fluorescence elemental analysis to the electro-deposited chemical species on the first electrode and generate spectroscopic data about the chemical species electro-deposited onto the first electrode after deposition; and a processor configured to use the spectroscopic data to determine the type and quantity of chemical species in the solution.

6. A sensor according to claim 5, wherein the electrical controller is configured to change the applied potential difference to strip the electro-deposited chemical species from the first electrode.

7. A sensor according to claim 6, wherein the electrical controller is configured to measure an electric current during stripping of the electro-deposited chemical species thereby generating voltammetry data for the electro-deposited chemical species, the first electrode functioning as an electrochemical sensing electrode and the second electrode functioning as a reference electrode.

8. A sensor according to claim 7, comprising a processor configured to use the spectroscopic data and the voltammetry data to determine the type and quantity of chemical species in the solution.

9. A sensor according to claim 7, wherein the second electrode is a non-fixed reference electrode and the spectroscopic data is used as an in-situ calibration for the voltammetry data.

10. A sensor according to claim 5, wherein the second electrode is formed of an electrically conductive diamond material.

11. A sensor according to claim 5, wherein the sensor comprises a window and the spectrometer is configured to direct the spectroscopic analysis technique through the window towards a front surface of the chemical species electro-deposited onto the first electrode.

12. A sensor according to claim 5, wherein the spectrometer is configured to direct the spectroscopic analysis technique through the first electrode towards a rear surface of the chemical species electro-deposited on the first electrode.

* * * * *